United States Patent [19]
Moore et al.

[11] 3,987,203
[45] Oct. 19, 1976

[54] ANESTHETIZING COMPOSITION AND METHOD

[75] Inventors: George L Moore, South Plainfield; Ross C. Terrell, Plainfield, both of N.J.

[73] Assignee: Airco, Inc., Montvale, N.J.

[22] Filed: Feb. 27, 1975

[21] Appl. No.: 553,857

Related U.S. Application Data

[62] Division of Ser. No. 341,909, March 16, 1973, Pat. No. 3,883,663, which is a division of Ser. No. 168,379, Aug. 2, 1971, Pat. No. 3,745,220.

[52] U.S. Cl. .............................................. 424/342
[51] Int. Cl.² ........................................ A61K 31/08
[58] Field of Search .................................. 424/342

[56] References Cited
OTHER PUBLICATIONS

Chemical Abstracts 54: 22484h–22485e (1960).

Crank et al., J. of Med. Chem., 1970, vol. 13, pp. 1215–1217.

*Primary Examiner*—Jerome D. Goldberg
*Attorney, Agent, or Firm*—Roger M. Rathbun; Edmund W. Bopp; H. Hume Mathews

[57] ABSTRACT

Aliphatic ether compounds of the formula

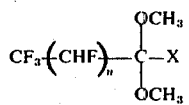

wherein $n$ is zero or one, and —X is —$CF_3$ or —H when $n$ is zero and is —$OCH_3$ when $n$ is one, are useful as inhalation anesthetics.

2 Claims, No Drawings

ANESTHETIZING COMPOSITION AND METHOD

This is a division of application Ser. No 341,909, filed Mar. 16, 1973, now issued U.S. Pat. No. 3,883,663, dated May 13, 1975, which in turn was divisional of application Ser. No. 168,379, filed Aug. 2, 1971, now U.S. Pat. No. 3,745,220, issued July 10, 1973.

This invention relates to certain aliphatic ether compounds and their use in producing anesthesia in anesthetic-susceptible mammals.

The compounds of the present invention have the formula

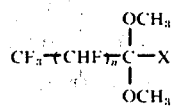

wherein $n$ is zero or one, and —X is —$CF_3$ or —H when $n$ is zero and is —$OCH_3$ when $n$ is one. These compounds lend themselves to effective use as inhalant anesthetics in respriable mixtures containing life-supporting concentrations of oxygen, with or without other inhalation anesthetics, such as nitrous oxide. Administration of the compounds may be by any of the well known techniques for administering general inhalation anesthetics, for example by using the open drip, semi-closed or closed systems.

The effective amounts of the compounds of this invention to be employed depend on the level of anesthesia to which the mammal is to be brought, the rate at which anesthesia is to be induced, and the length of time over which anesthesia is to be maintained. Minor volume percentages of the compound in oxygen can often be employed. The amount used should be sufficient to provide a significant anesthetic effect, but not so much as to produce unacceptable deleterious side effects. Vapor concentrations at which the compounds of this invention may often be used are about 0.5 to 6 volume percent, with the concentration actually employed depending on the choice of anesthetic; for instance, 1,1,1,2-tetrafluoro-3,3,3-trimethoxypropane may often be used in an amount of about 0.5 to 2.8%, trifluoroacetaldehyde dimethyl acetal may often be used in an amount of about 2 to 6%, and dimethylketal of hexafluoroacetone may often be used in an amount of about 3 to 6%. The amount of anesthesia to be used can be regulated, starting with a small amount of the ether and gradually increasing the amount until the desired plane of anesthesia is reached. By then monitoring the physical reactions of the mammal, as is the usual procedure, the duration and plane of anesthesia can be readily controlled.

The compounds of this invention are also easily miscible with other organic liquids, including fats and oils, and have useful solvent properties, for example as solvents for fluorinated olefins and other fluorinated materials, such as fluoro waxes. The compounds of this invention may be used to prepare pastes and dispersions of such materials useful for coatings and the like, and may be used as degreasing agents. In the latter capacity, for example, the ether compounds of this invention can be used as solvents to remove grease or other oily substances from metal surfaces that are to be painted.

The following examples illustrate the preparation of the compounds of the present invention.

EXAMPLE I

This example illustrates the preparation of 1,1,1,2-tetrafluoro-3,3,3-trimethoxypropane.

Perfluoropropene (48.7 g.) was added slowly to a cold (0°–5° C.) solution of $NaOCH_3$ (35.2 g.) in methanol (140 ml.) over a period of 1 hour, followed by warming at 55° C. for 5 hours. The mixture was poured into water and neutralized, and the crude product was isolated by refluxing the aqueous mixture into a Dean-Stark tube. Fractional distillation of the dried (over $K_2CO_3$) product gave a fraction boiling at 95°–100° C. from which $CF_3CHFC(OCH_3)_3$ was obtained by preparative chromatography.

This normally liquid ether has a boiling point of 118° C., a specific gravity of 1.27, a vapor pressure at 25° C. of 21 mm. Hg., a refractive index ($n_D^{20}$) of 1.3497, and a mild odor. The compound is nonflammable.

EXAMPLE II

This example illustrates the preparation of the dimethylketal of hexafluoroacetone.

Hexafluoroacetone (43 g.) was added to methanol (7.5 g.) at −40° C. followed by warming the mixture to room temperature. Diethyl ether (60 ml.) and dimethylsulfate (35.7 g.) were added, followed by gradual addition of anhydrous, granular $K_2CO_3$ (43 g.). The mixture was stirred for 7.5 hours. The mixture was diluted with water followed by extracting with diethyl ether. Ether was stripped from the dried ($K_2CO_3$) extract leaving a crude product from which 27 g. of pure $(CF_3)_2C(OCH_3)_2$ was obtained by preparative chromatography.

Calculated for $C_5H_6F_6O_2$ : F, 53.8% Found : F, 53.9%.

This normally liquid compound has a boiling point of 85° C., a specific gravity of 1.34, a vapor pressure at 25° C. of 80 mm. Hg., a refractive index ($n_D^{20}$) of 1.3054, and a faint, sweet odor. It is nonflammable.

EXAMPLE III

This example illustrates the preparation of trifluoroacetaldehyde dimethyl acetal. Anhydrous, granular $K_2CO_3$ (43 g.) was added gradually to s solution of commercially obtained trifluoroacetaldehyde methyl hemiacetal (34 g.) and dimethylsulfate (36 g.) in diethyl ether at 20°–25° C. followed by stirring for 10 hours. The mixture was poured into water, then extracted with diethyl ether. Diethyl ether was stripped from the dried (over $K_2CO_3$) extracts, and pure $CF_3CH(OCH_3)_2$ (15 g.) was separated from the crude product by preparative chromatography.

Calculated for $C_4H_7F_3O_2$ : F, 39.6% Found : F, 39.3%.

This normally liquid compound has a boiling point of 78.5° C., a specific gravity of 1.28, a vapor pressure at 25° C. of 110 mm. Hg., and a refractive index ($n_D^{20}$) of 1.3222. The compound is flammable.

In order to determine the potency of the aliphatic ethers of the present invention as inhalation anesthetics in combination with oxygen, tests were carried out on mice. The compounds tested were at least 99.5% pure as determined by vapor phase chromatography. In the tests, the ether compound is administered to test mice by a standard procedure in which a measured quantity of the agent is placed on a laboratory jar and allowed to completely vaporize so as to give a calculated vapor concentration. The test mice are then quickly placed in the jar and observed. Anesthesia is determined by observing the righting reflex of the mice. Recovery time is measured beginning when the mice are transferred from the test jar to room air and ending when the mice are observed to be able to walk.

In such tests the 1,1,1,2-tetrafluoro-3,3,3-trimethoxypropane induced anesthesia in the mice in 1 minute when used at a vapor concentration of 1%. Induction was smooth, but there were bursts of rapid limb tremors—sometimes one limb only—throughout maintenance of the anesthesia. These tremors, which at times had the appearance of a focal convulsion, continued with much squeaking for 3 minutes into the recovery period, which lasted 4 minutes 35 seconds. Some analgesia was evident during anesthesia. When used at 2% vapor concentration, essentially the same results were observed, except that the induction period was shortened to 25 seconds and the recovery period was lengthened to 7 minutes 31 seconds.

Use of 4% vapor concentration of the dimethylketal of hexafluoroacetone resulted in induction of anesthesia in 1 minute 10 seconds. The induction was accompanied by much excitement. The anesthesia was light and the mice responded to stimulation while under it. When 5% vapor concentration was used, a deeper anesthesia was induced in 49 seconds; recovery required 1 minute 34 seconds.

The acetal, dimethyl acetl, when used at 2.5% vapor concentration, induced a light anesthesia in 2 minutes 13 seconds. An uneventful recovery therefrom occurred in 30 seconds. At 4.0% vapor concentration, the induction time was shortened to 1 minute 11 seconds and the recovery time was lengthened to 2 minutes 8 seconds. Some analgesia was evident along with the anesthesia.

While there has been described what are at present considered to be the preferred embodiments of the invention, it will be understood that various modifications may be made therein which are within the true spirit and scope of the invention.

I claim:
1. An inhalant anesthetic composition comprising an anesthetically-effective amount of an aliphatic ether compound of the formula

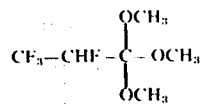

and oxygen.

2. A method of anesthetizing an anesthetic-susceptible mammal which comprises administering to the mammal an anestheticlly-effective amount of an aliphaic ether compound of the formula

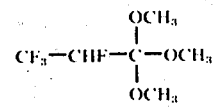

as an inhalation anesthetic, while administering life supporting amounts of oxygen.

* * * * *

UNITED STATES PATENT AND TRADEMARK OFFICE
CERTIFICATE OF CORRECTION

PATENT NO. : 3,987,203
DATED : October 19, 1976
INVENTOR(S) : George L. Moore & Ross C. Terrell It is certified that error appears in the above–identified patent and that said Letters Patent are hereby corrected as shown below:

Col. 1, line 23, "respriable" should be -- respirable --.

Col. 2, line 44, "s" should be -- a --;

line 66, "on" should be -- in --.

Col. 3, line 29, "acetal" should be -- trifluoroacetaldehyde -- and "acetl" should be -- acetal --.

Col. 4, line 23, "anestheticlly" should be -- anesthetically --.

Signed and Sealed this

Fourth Day of January 1977

[SEAL]

Attest:

RUTH C. MASON
Attesting Officer

C. MARSHALL DANN
Commissioner of Patents and Trademarks